United States Patent [19]

Stephens, Jr. et al.

[11] Patent Number: 5,061,241

[45] Date of Patent: Oct. 29, 1991

[54] RAPID INFUSION DEVICE

[76] Inventors: Harry W. Stephens, Jr., 2340 Riverbend Rd., Allentown, Pa. 18103; Norman J. Manley, 967 Chris La., Allentown, Pa. 18105; Ralph M. Montesano, 2737 Rt. 100, Macungie, Pa. 18062

[21] Appl. No.: 652,481

[22] Filed: Feb. 8, 1991

Related U.S. Application Data

[63] Continuation of Ser. No. 299,099, Jan. 19, 1989, abandoned.

[51] Int. Cl.$^5$ .............................................. A61F 7/12
[52] U.S. Cl. .................................... 604/114; 604/118; 604/122; 604/406; 137/539
[58] Field of Search ....................... 604/4, 7, 113, 114, 604/118, 122, 123, 151–153, 128, 129, 257, 259, 282, 319, 405, 406; 132/115, 539

[56] References Cited

U.S. PATENT DOCUMENTS

| | | | |
|---|---|---|---|
| 2,307,949 | 1/1943 | Phillips | 137/539 |
| 2,742,054 | 4/1956 | Poundstone | 137/539 |
| 4,115,277 | 9/1978 | Swank | 210/436 |
| 4,196,729 | 4/1980 | Nathan et al. | 604/118 X |
| 4,228,125 | 10/1980 | Lobdell et al. | 422/46 |
| 4,261,360 | 4/1981 | Perez | 604/123 X |
| 4,368,118 | 1/1983 | Siposs | 210/136 |
| 4,440,722 | 4/1984 | Luppi | 422/46 |
| 4,526,515 | 7/1985 | DeVries | 417/63 |
| 4,531,941 | 7/1985 | Zasuwa | 604/113 |
| 4,572,724 | 2/1986 | Rosenberg et al. | 55/159 |
| 4,678,460 | 7/1987 | Rosner | 604/113 |
| 4,705,508 | 8/1987 | Karnavas et al. | 604/113 |
| 4,707,587 | 11/1987 | Greenblatt | 219/299 |
| 4,747,826 | 5/1988 | Sassano | 604/52 |

FOREIGN PATENT DOCUMENTS

| | | |
|---|---|---|
| 0174420 | 3/1986 | European Pat. Off. |
| 0234713 | 9/1987 | European Pat. Off. |
| 0292399 | 11/1988 | European Pat. Off. |
| 2188392 | 1/1974 | France . |
| 2513884 | 4/1988 | France . |

*Primary Examiner*—John D. Yasko
*Assistant Examiner*—Adam J. Cermak
*Attorney, Agent, or Firm*—James A. Wong

[57] ABSTRACT

The Rapid Infusion Device is a mechanical pumping system for the rapid delivery of filtered, bubble free, warmed volume to a patient suffering from acute hypovolemia. The principle of operation is one of overcoming resistance mechanically, The flow of fluids is totally regulated by the resistance encountered at the smallest tubing orifice along the infusion pathway. The RID components, assembled as a system, provide the capability for the rapid infusion of filtered, bubble free, and warm volume. The word volume is used to describe the fluid delivered by the device as any desired fluid may be delivered by the device. The RID is composed of two systems, i.e., durable permanent equipment and a disposable unit for one time use. Durable equipment consists of a roller pump, its controls, a permanently mounted heating element and its controls, and a mounting bracket to attach the heating element to the housing of the roller pump. The disposable unit is made of molded plastic cast in two halves. All of the sub-components of the disposable unit are installed at the manufacturing stage and before the two halves are joined, adhered and sealed for liquid integrity.

8 Claims, 9 Drawing Sheets

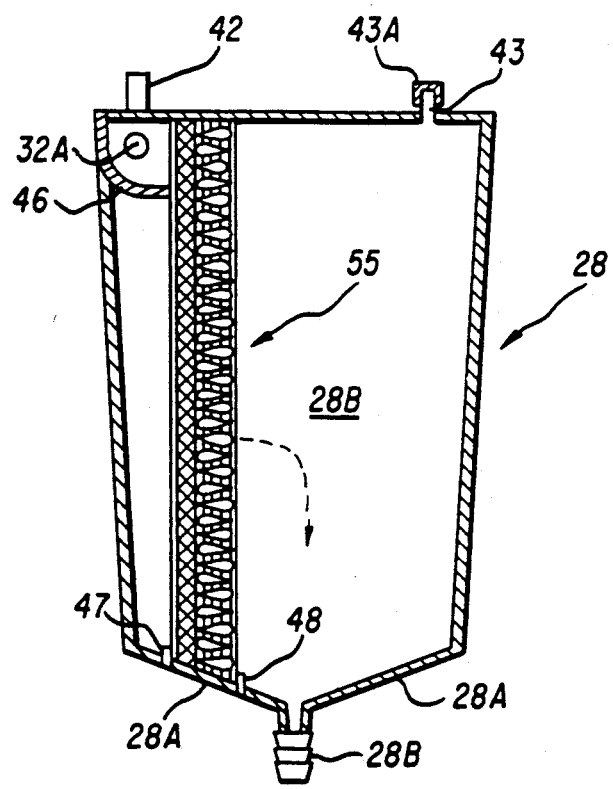
FIG. 5
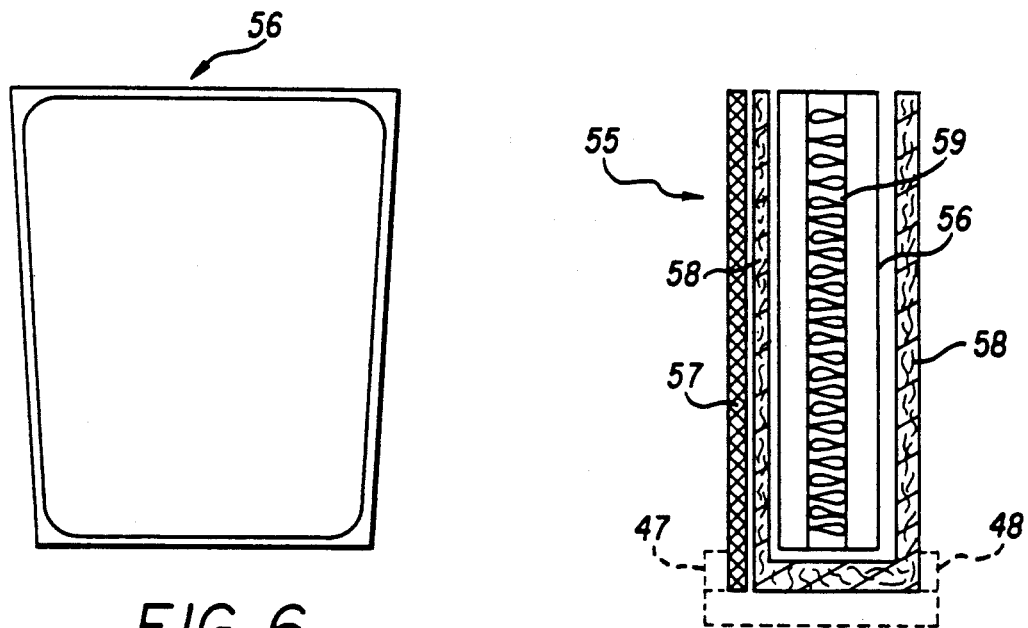
FIG. 6
FIG. 7

RAPID INFUSION DEVICE

This is a continuation of co-pending application Ser. No. 299,099, filed on Jan. 19, 1989, now abandoned.

TECHNICAL FIELD

This invention relates to an apparatus for the rapid infusion of circulatory supportive fluids such as blood into a patient. The apparatus comprises both durable or permanent components and disposable sub-components. The disposable sub-components include various components which physically come into contact with the fluid being infused. The principal advantage achieved from this arrangement resides in the fact that after each use, the disposable components are destroyed and replaced with new sterile components to preclude contamination from patient to patient as well as from medical personnel to patient.

BACKGROUND OF THE INVENTION

During surgery or in the emergency room, it is frequently necessary to infuse blood rapidly into a patient, particularly when massive blood losses have occurred. Patients having inadequate blood volume can suffer serious consequences.

There are many situations where large amounts of blood can be lost in a very short period of time, for example, in cases of serious automobile accidents, gun shot wounds in critical areas of the body, and a variety of major surgery including cancer surgery and heart and liver transplants.

In the past, the replacement of large amounts of blood loss has been a major problem to the surgical teams attending a suffering patient. A common method of rapid infusion includes the use of a plurality of infusion sites simultaneously. Infusion bags or bags of stored banked blood are interconnected by intravenous tubing. Frequently, a plurality of medical personnel are required to oversee the various infusion sites and to personally ensure the flow of blood from the blood bags or monitor the pumps which infuse the blood to the patient.

It is also well known that the temperature of the blood to be infused into a patient is a critical item which must be monitored closely. In this regard, to maintain the infused blood at the desired temperature, various arrangements of heating coils have been strategically placed around the infusion, thus increasing the complexity of arrangement and requiring additional personnel to ensure successful operation.

It can readily be seen that from the foregoing, that any apparatus which would satisfy the various requirements of rapid infusion while at the same time reducing the number of medical and/or technical personnel required to monitor the equipment would be a much desired improvement over presently known systems and practices used in such critical life threatening situations.

SUMMARY OF THE INVENTION

With knowledge of the shortcomings of present day blood infusion apparatuses noted above, applicants have been motivated to develop the rapid infusion device disclosed and claimed in the instant application. The rapid infusion device, referred to hereinafter as RID, is composed of two systems. One system includes durable equipment, i.e., equipment which can be used over and over again, such as the roller pump and its related controls, a permanently mounted heating element and its related controls, and mounting bracket structure for attaching the heating element to the housing of the roller pump. The other systems include the disposable components of the RID such as the blood reservoir, the three stage filter insert, aluminum-telfa interior wall of the heating unit, two-way valves and a spring loaded pressure control valve. Additionally, all volume pathways are cast as a part of a disposable unit housing. A disposable length of one quarter inch PVC tubing is also provided to connect the filter-reservoir to the heating unit.

The disclosed Rapid Infusion Device is a mechanical pumping system for rapidly delivering filtered, bubble-free, warmed blood to a patient suffering from acute hypovolemia. The principle of operation of the disclosed invention is one of overcoming resistance mechanically. The flow of fluids is totally regulated by the resistance encountered at the smallest tubing orifice along the infusion pathway. The word volume is used to describe or refer to the fluid delivered by the device as any desired fluid other than blood may also be delivered by the device.

The RID provides an apparatus for the rapid infusion of volume being pumped. Additionally, the RID provides a means of de-aerating the volume and also a heating means for maintaining the volume at the desired temperature. The pump utilized is a variable speed unit so that the amount of volume being pumped in can be increased merely by increasing the rpm of the pumping unit. The reservoir contains plural stages of filters and is provided with a plurality of inlets whereby volume from multiple sources can be fed into the reservoir to satisfy any high demand requirements of a patient. As set forth above, the RID comprises a permanent system and a disposable system. The disposable system includes all the components with which the volume comes into direct contact. The disposable aspect of the invention provides an extra measure of protection against contamination to a subsequent patient.

With the foregoing in mind, it is a primary object of the present invention to provide an apparatus which is capable of high volume pumping.

Another object of the invention is to provide an apparatus having a permanent system and a disposable system.

A further object of the invention is to provide a RID in which the disposable portion includes all components which come into direct contact with the volume being infused.

Yet another object of the invention is to provide an apparatus which de-aerates and heats the volume being infused.

Still another object of the invention is to provide an apparatus which is compact, multi-functional, and capable of operation by a single person.

A further object of the invention is to provide a RID which includes a multi-filter arrangement for cleansing the volume prior to infusion.

Another object of the invention is to provide a RID which also includes a pressure control valve for regulating system pressure and, more specifically, infusion pressure to the patient.

Other objects and advantages of the instant invention, in addition to those set forth above, will become more apparent from the ensuing detailed description considered in conjunction with reference to the accompanying drawings which form a part of this specification wherein like reference characters designate corresponding parts in the several views.

BRIEF DESCRIPTION OF THE DRAWINGS

Referring briefly to the drawings, the reader will readily appreciate that:

FIG. 5 is a sectional view of the filter/reservoir taken along the line 5—5 of FIG. 4;

FIG. 6 is an elevational view of the filter frame per se;

FIG. 7 is a sectional view of the filter illustrating the plurality of layers;

DETAILED DESCRIPTION OF THE DRAWINGS

Figure 1:
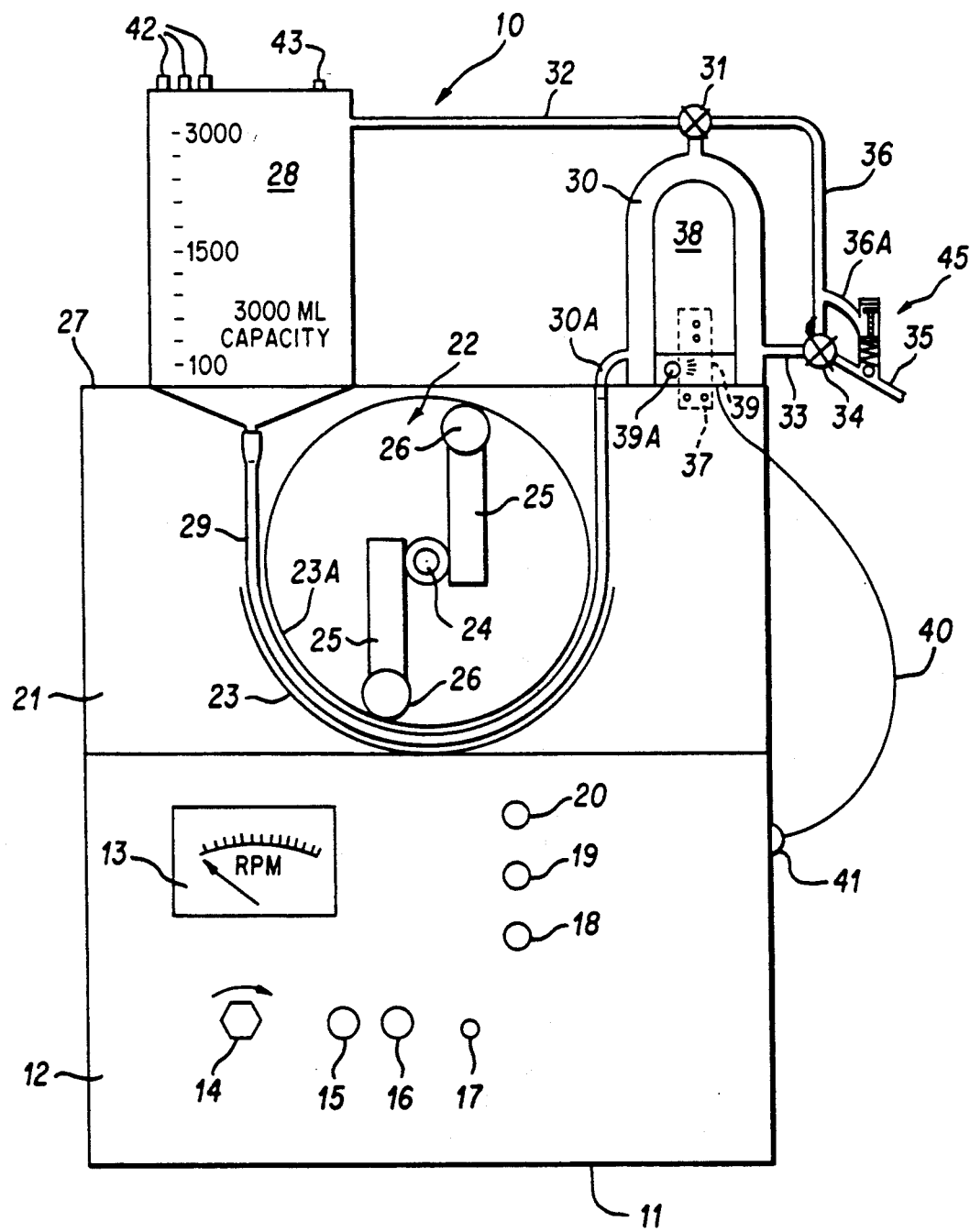
FIG. 1 is a front elevational view of the rapid infusion device.

Referring now in detail to FIG. 1, the reader will see from the front elevational view of the disclosed invention that the rapid infusion device generally indicated by reference numeral 10 comprises a base portion 11 which houses a control panel 12 having a tachometer 13, rpm control knob 14, AC power fuse 15, DC power fuse 16, and on/off switch 17. On the upper right portion of control panel 12 are located AC/DC selector switch 18, stop/forward switch 19 for a motor (not shown) for driving roller pump 22. Above stop/forward switch 19 is located the reverse switch 20 for reversing the rotation of roller pump 22.

Mounted on top of control panel 12 is pump housing 21 which serves as the mounting support for roller pump 22 and its drive motor (not shown). Roller pump 22 comprises a pair of walls 23, 23A forming a raceway, which tubing 29 is inserted into and supported thereby. A pair of roller support arms 25 extend from shaft 24, each of which supports a roller 26 at the distal end thereof for engagement with tubing 29. Each of the support arms 25 extend in opposite directions with respect to each other from shaft 24.

Mounted on upper surface 27 of pump housing 21 are the various components of the disposable unit including filter/reservoir 28, heat exchange component 30 and associated tubing line 29 leading from filter/reservoir 28 to roller pump 22 which discharges pumped volume to heat exchange component 30 which is in the form of an inverted U-shaped member. The upper portion of heat exchange component 30 is interconnected with two-way purge by-pass valve 31 which connects with purge by-pass line 32 back to filter/reservoir 28. The right leg of heat exchange component 30 includes an outlet line 33 which connects with the by-pass to patient two-way valve 34. The left leg of heat exchange component 30 includes an inlet stem portion 30A for connection with line 29. Two-way valve 34 can be set to direct pumped volume to either patient line 35 or purge by-pass line 36 back to filter/reservoir 28.

Bracket 37, which is shown in dashed lines, serves as the mounting bracket for permanent heating element 38. Thermostatic control of permanent heating element 38 is provided by knob 39 for controlling the temperature of the volume. Extending from the base of permanent heating element 38 is electrical cord 40 provided with plug 41 which is plugged into control panel 12 and thereby supplies electrical current to permanent heating element 38. As indicated above, the device 10 is provided with AC and DC controls in the event that there is a power failure or the device 10 is to be used in an area where AC power is not available.

Figure 2:
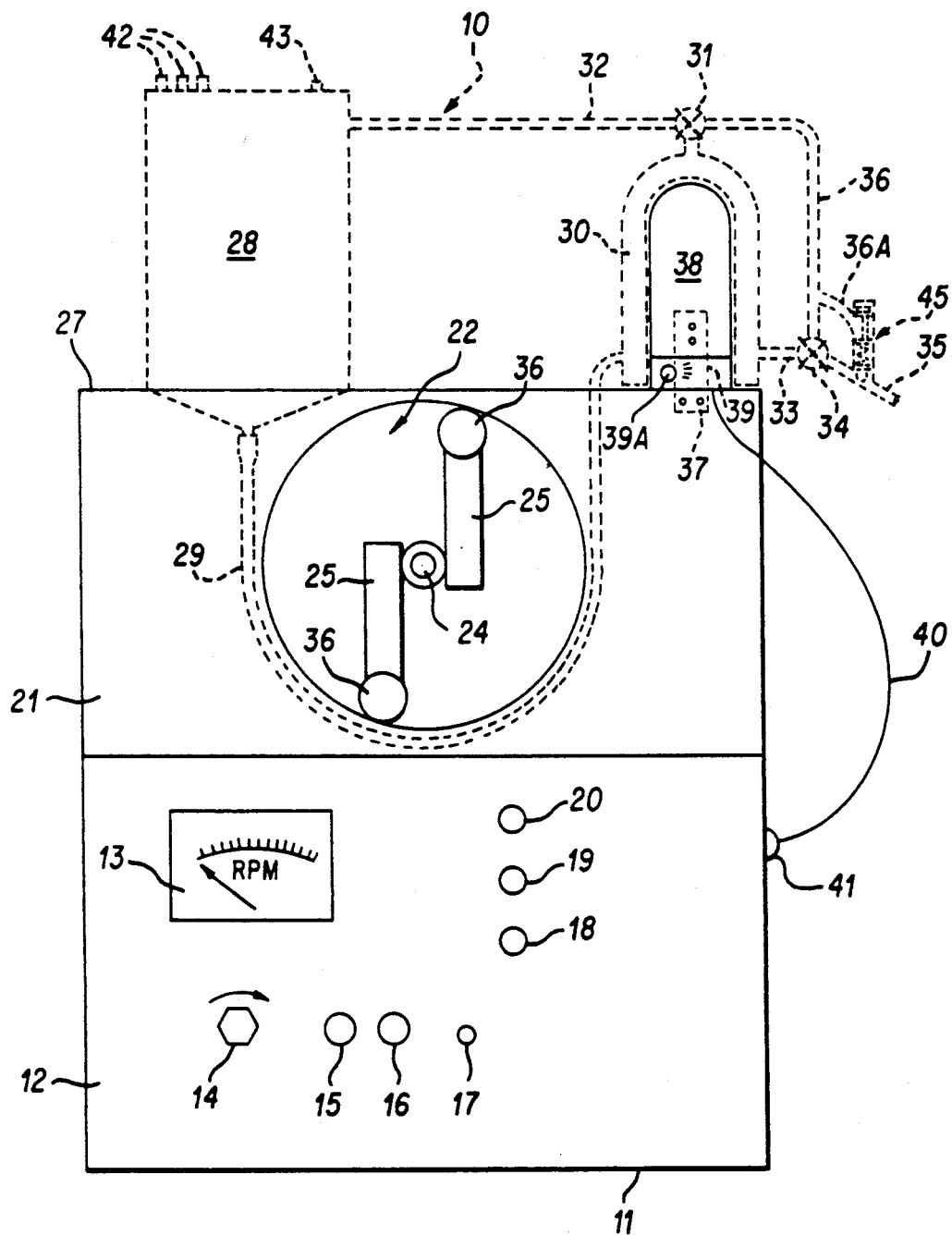
FIG. 2 is also a front elevational view of the rapid infusion device in which all of the disposable components are shown in broken lines.
Figure 4:
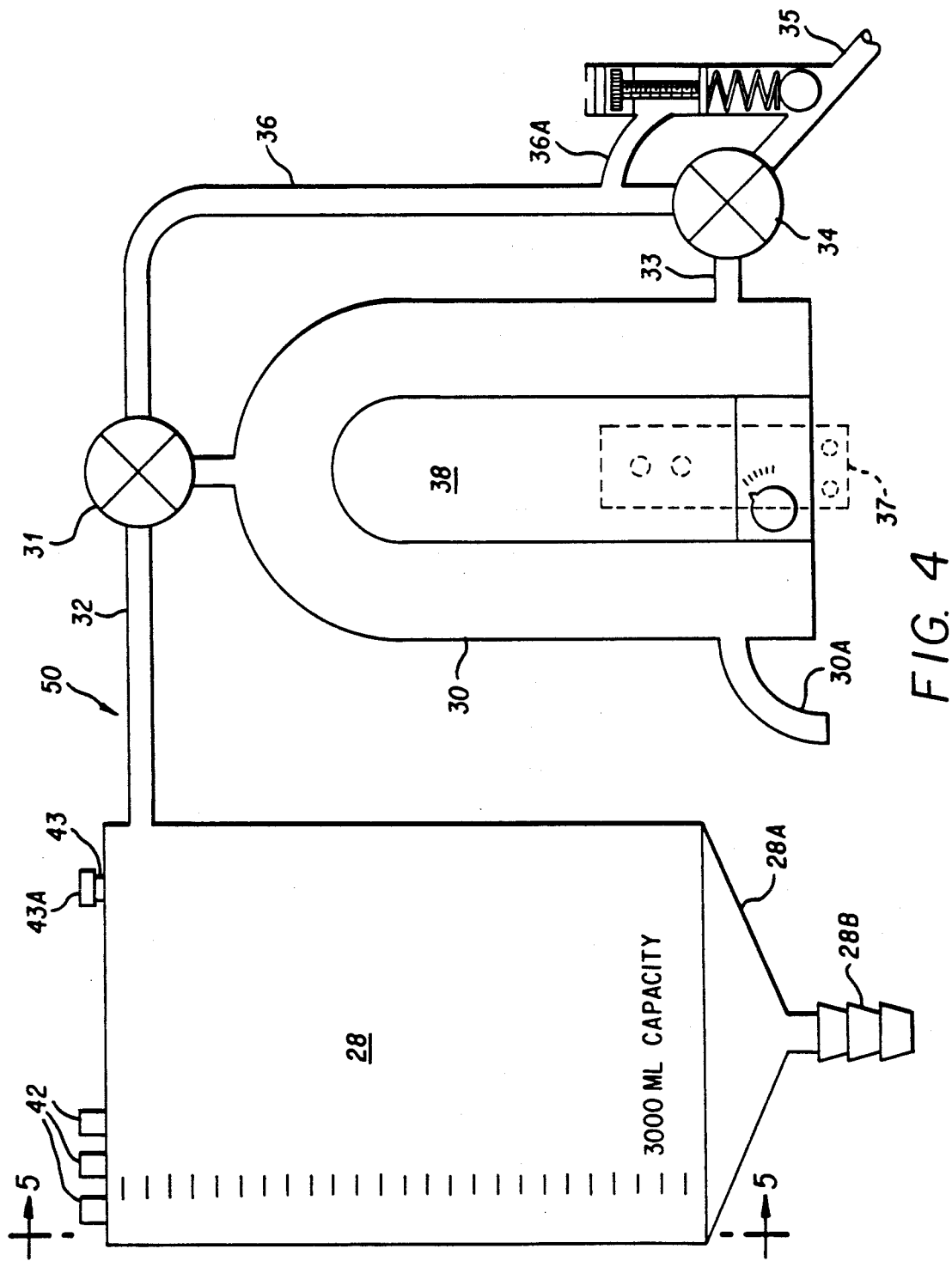
FIG. 4 is a front elevational view of the durable heating element along with the disposable components per se.

Referring now to FIG. 2, the reader can readily see basically showing the same structure illustrated in FIG. 1, but with the entire disposable system shown in dashed lines in FIG. 2. As illustrated, filter/reservoir 28 is provided with a plurality of fluid inlet ports 42 to enable rapid replenishment of the volume in filter/reservoir 28. Additionally, air vent 43 is shown at the upper right corner of filter/reservoir 28 with vent cap removed. FIG. 2 provides a complete view of all the disposable components. The disposable components illustrated provide pathways for volume in the various operating modes of the system. The disposable unit provides access to the system through its three inlet ports 42. The volume to be pumped through the system may be pumped, poured, or drained into the filter/reservoir 28 through ports 42. Temporary storage, filtration, heating and the direction of volume flow is controlled by the disposable unit. System pressure is regulated in the unit by the spirng loaded pressure control valve 45. De-aerating of volume is accomplished by removing the cap on air vent 43 to allow the passage of air in and out of the system and the positioning of the purge by-pass two-way valve 31. When venting is not desired, air vent 43 is closed by cap 43A thereover as illustrated in FIGS. 4 and 5. Flow to the patient and alternative by-pass route for volume is achieved in the unit by setting the by-pass-to-patient two-way valve 34 in the desired position provided for in FIGS. 11-14.

The disposable unit combines the filter/reservoir 28 with its filtration function, heat exchange component 30, two directional control valves 31 and 34 and the system pressure regulating control valve 45 into one unit. This unit is disposable as it comes in contact with volume and is considered potentially contaminated and not to be re-used. All parts of the system coming in contact with either volume or patient are disposable, including the PVC connecting line 29 between the filter/reservoir 28 and heater unit 30 and the catheter (not shown) connected to line 35 to the patient for infusing the patient.

Figure 3:
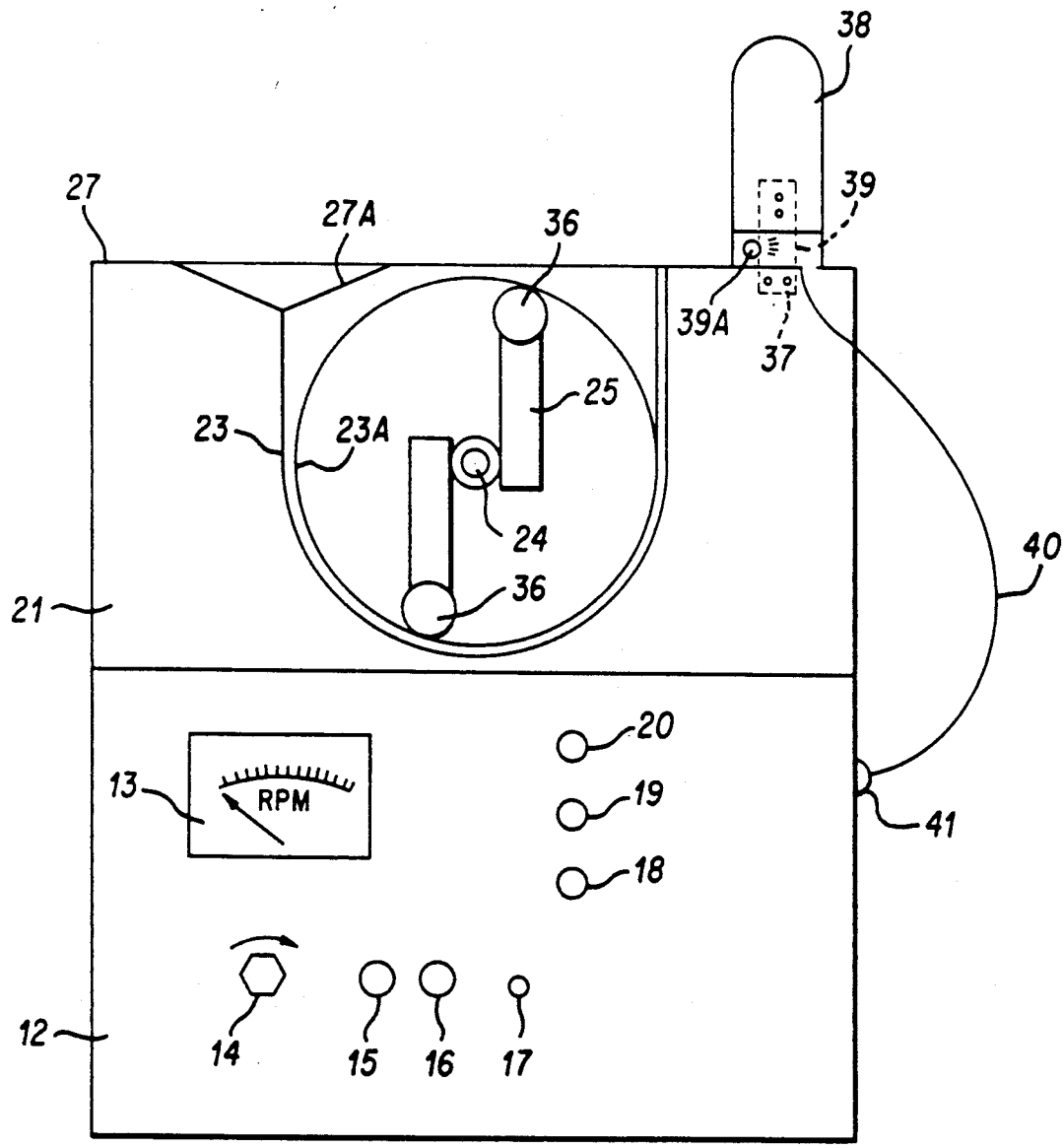
FIG. 3 is a front elevational view illustrating the durable or permanent non-disposable components of the device.

Referring now to FIG. 3, the reader can readily see the durable or permanent non-disposable components of RID 10 with the relationship of the permanent components such as heating element 38, its supporting bracket 37 which serves as its mount, and thermostat 39 with its control knob 39A. Additionally, conical recess 27A, which receives and supports the generally conical or frustoconical lowermost portion 28A of the filter/reservoir 28 when inserted therein, is readily seen. Omitted from FIG. 3 is tubing line 29 which is normally disposed in the raceway formed by walls 23 and 23A since tubing line 29 is removed as with the parts of the disposable unit.

Referring now to FIG. 4, there is illustrated a complete showing of the disposable unit 50 of the RID 10 and its relationship to permanent heater element 38. The only two disposable items not illustrated here are the piece of PVC tubing 29 which interconnects fitting 28B of filter/reservoir 28 with stem 30A of heater unit 30 and the catheter (not shown) which connects with line 35 to the patient.

Disposable unit 50 shown in FIG. 4 in operation provides filtration of volume in filter/reservoir 28, acts as a vessel to provide temporary storage volume in the reservoir 28, and provides a controlled pathway for volume to flow, when valves 31 and 34 are set in their desired positions. Heat exchange is also accomplished in disposable unit 50 by way of the relationship of heat exchange component 30 with permanent heating element 38.

The housing of the disposable unit 50 is made of plastic, molded in two halves, filters, valves and the aluminum-telfa interior wall of the heating unit 30, are installed and the halves are then joined, adhered and sealed for liquid integrity. The disposable unit 50 is designed for a single use and is destroyed thereafter. Similarly, all other pathways coming into direct contact with volume are disposed of and/or destroyed, a safety feature to avoid possible contaminaton of the disposable unit 50 and other volume pathways. Other volume pathways include all PVC lines 29 and 35 used in the device. Although permanent heating element 38 is illustrated in FIG. 4 to show its relationship with the disposable unit 50, it is a durable permanent part of RID 10 and is mounted on pump housing 21 via bracket 37.

Referring now to FIG. 5, there is illustrated a cross-sectional view taken along the line 5—5 of FIG. 4 showing one of the three inlet ports 42 since the other two inlet ports 42 are hidden by first inlet port 42. There is also shown the inlet port 32A for purge by-pass line 32. Baffle 46 is located in the upper left interior corner of filter/reservoir 28 and extends the full width thereof. Filter 55 is shown standing vertically in filter/reservoir 28. At the left conical portion 28A, a pair flanges 47 and 48 project upwardly therefrom permitting filter 55 to rest therebetween and retained thereat on the left of conical portion 28A.

Filter/reservoir 28 provides another safety feature with the added function of storing volume to be infused into the patient. In a preferred embodiment of the invention, the capacity of the vessel is 3000 ml. The baffle 46 is molded into the filter/reservoir 28 housing during manufacturing and functions to create a vortex minimizing any effect which flow may have on the volume to be infused. The baffle 46 directs the incoming volume into the coarse side of the filter 55. The air vent 43 in filter/reservor 28 is operated by loosening screw cap 43A on vent 43 to allow air to enter and leave RID 10. By-pass inlet port 32A allows for the return of volume to filter/reservoir 28 when the device is being purged of air, operated in the by-pass mode and when pressure to the patient has become great enough to open the spring pressure control valve 45.

FIG. 6 shows details of the filter frame 56 per se which has the purpose of holding the Cottonow "3" material 59 which is part of the three layered second stage of filter 55.

Referring now to FIG. 7, there is shown a two stage filtration system including a first stage with a layer of coarse sponge plastic material 57 which is positioned on the fill side of the filter/reservoir 28 and functions to remove material in the volume of over 100 to 150 microns in size. The coarse filter material 57 is compressed against the next three layers of filter material in which fine filtration takes place.

In the second stage, fine filtration functions to remove any remaining impurities in the volume of 27 to 40 microns in size. Fine filtration of volume is achieved by passage through three layers of filter material, including a first layer of nylon mesh 58, followed by Cottonow "3" material 59, and a second layer of nylon mesh 58. As fine filtration takes place, volume is passed into front reservoir chamber 28B for circulation in the system. The filter 55 is assembled by inserting Cottonow filter material 59 in the center of the frame 56. A fine nylon mesh "sock" 58 fused into two sides is slipped over the frame 56 containing the Cottonow material 59, forming three layers. The coarse layer 57 of filter material is then applied to the frame 56 to complete the wafer effect. Coarse layer 57 is made of plastic sponge material woven in a matrix to prevent particles in excess of 150 microns from passing through it. After the frame 56 is assembled with filter media, it is installed and sealed in the filter seat formed by seat flanges 47 and 48.

Figure 8:
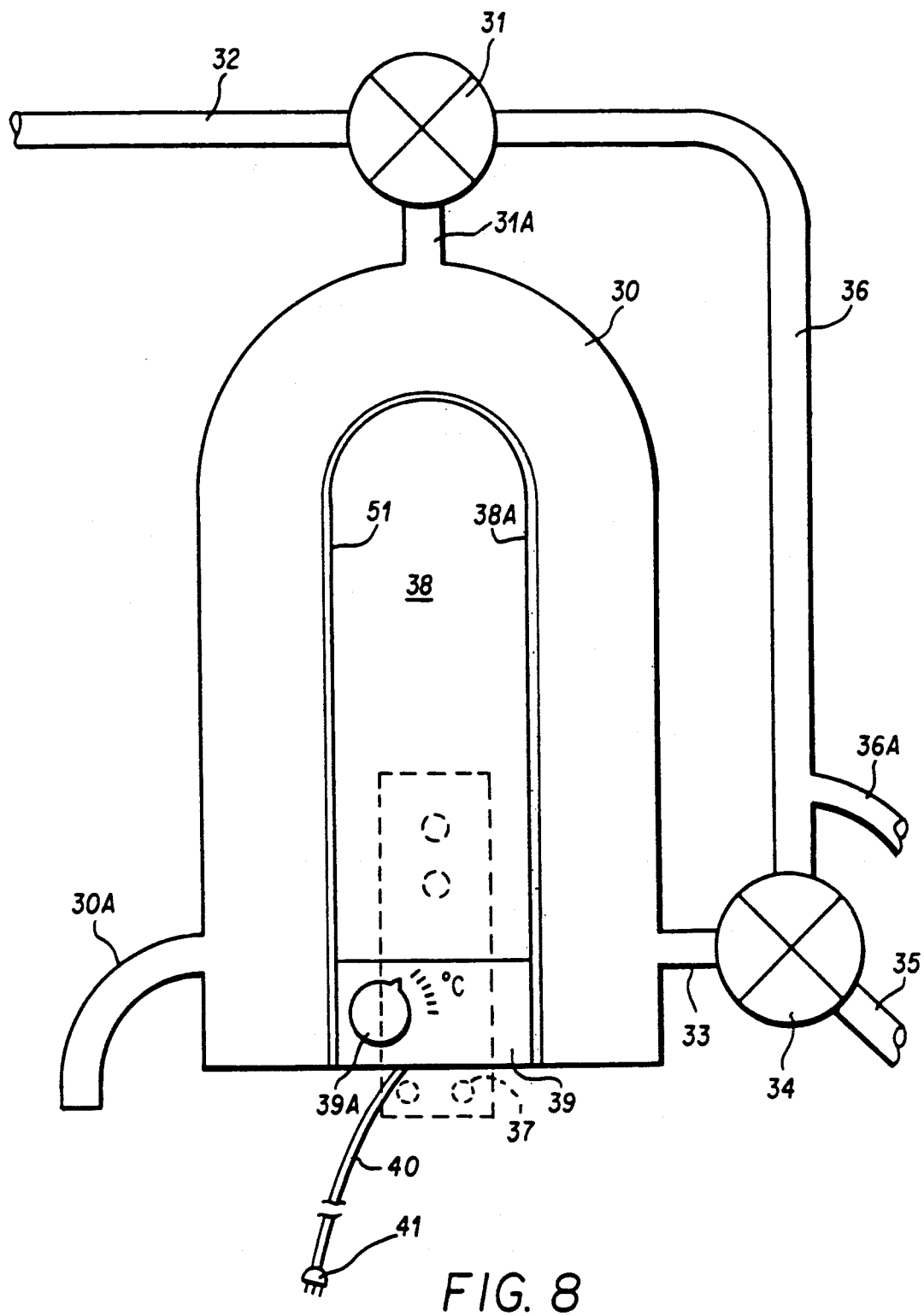
FIG. 8 is an illustration of the disposable heating unit assembled with the durable or permanent heating element.

Referring now to FIG. 8, heat exchange component 30 may be seen with its various connections 30A, 33, and 31A to the various pathways of the system. As illustrated, heat exchange component 30 includes a hollow interior to permit the passage of volume therethrough and is shaped in the form of an inverted-U. The inverted-U member is made of an aluminum alloy with the inner wall 51 coated with aluminum-telfa to assist in the conduction of heat from heating element 38 to heat exchange component 30 and thence to the volume flowing therethrough. The exterior aluminum wall 38A of the heating element 38 and the interior wall 51 of heat exchange component 30 are disposed in a male-female relationship.

Heat exchange component 30 receives its volume supply from roller pump 22 which has created the flow for the entire system. As volume flows through heat exchange component 30, heat exchange between volume and the walls 38A and 51 takes place and recirculated volume is heated to a pre-set temperature by the setting of thermostat control knob 39A. The heater element 38 is heated by 115 volts, AC current via grounded cord 40 plugged into an accessory outlet on the control panel 12. The heat exchange component 30 is considered to be another safety feature, as infusing volume to a patient under 37 degrees C., can cause the patient to go into a state of shock.

Figure 9:
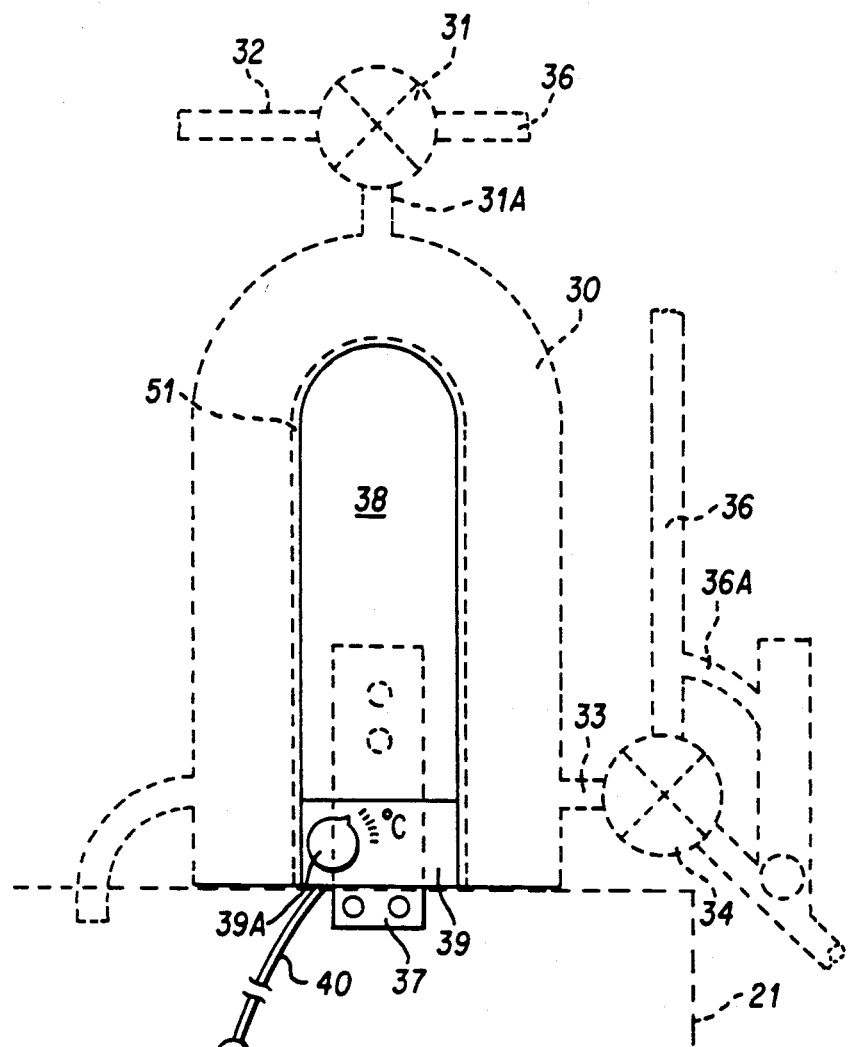
FIG. 9 is an elevational view similar to FIG. 8, but with the disposable components illustrated in broken lines.

Turning now to FIG. 9, the heat exchange component 30 and the pump housing 21 may be seen in dashed lines. Heating element 38 has an upper arched portion which conforms to U-shaped configuration of heat exchange component 30. Thermostat 39 may be seen with control knob 39A for setting the desired temperature in FIG. 9. As pointed out earlier, heating element 38 and thermostat 39 are durable components of the RID 10.

Figure 10:
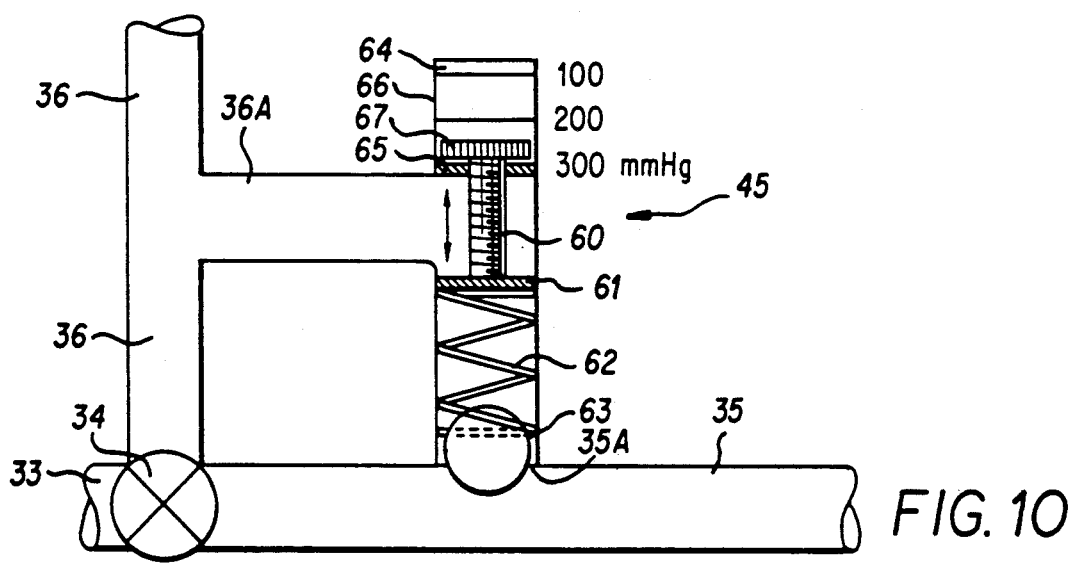
FIG. 10 is an enlarged detail view of the spring loaded pressure control valve.

Spring loaded pressure control valve 45, which may be seen in FIG. 10, provides another of the enumerated safety features of the RID 10. As shown, pressure control valve 45 comprises a threaded screw 60 which is threaded into stationary disc 65. Extending upwardly above valve 45 is a graduated cylindrical housing 66 with a removable cap 64 thereon to permit access to the screw head 67 which is provided with a slot (not shown) in its upper surface to receive a screwdriver to make the necessary adjustment to the valve 45. Attached to the lowermost end of screw 60 is a perforated base disc 61 which biases spring 62 into engagement with ball 63. Disc 61 is perforated to permit volume to flow therethrough when ball 63 is unseated from seat 35A.

The function of valve 45 is to regulate system pressure and, more specifically, infusion pressure to the patient. As can be seen, valve 45 includes a spring loaded, adjustable ball valve 63 which seats on seat 35A, with helical spring 62 having a known resiliency that can be adjusted with compression. When the screw 60 is advanced, compression on the spring 62 is increased and when withdrawn, decreased. The adjustable limits of the valve 45 are limited by the distance the adjusting screw 60 can travel in its housing 66. An adjustable range of 100 to 300 mm Hg is provided and access to the adjustment screw 60 is obtained through the access port when cap 64 is removed. The normal setting for valve 45 is in the range of 230–300 mm Hg, but may be changed depending on the body size of the patient or any other variable which may indicate that a change in pressure is desirable.

The pressure control valve 45 is positioned as near as possible to the patient to sense an overpressure condition. When such a condition exists, the valve 45 will open by unseating from seat 35A and volume will escape around the ball 63 through perforations in disc 61 and back through the system in the pathways 36A, 36, and 32. The illustrations of the valve 45 are not intended to be "as built" drawings, but rather to indicate its position and general construction characteristics.

Figure 11:
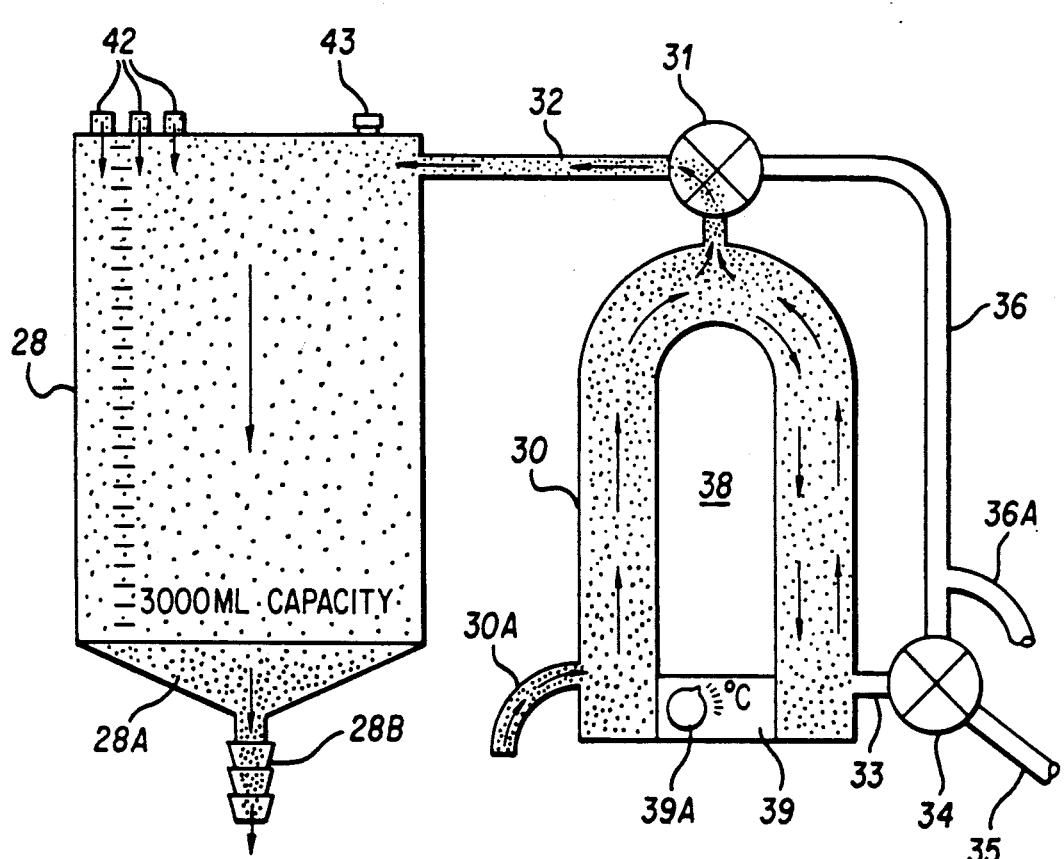
FIG. 11 illustrates the flow of volume in the purge mode of operation.

FIG. 11 is the first of four figures depicting the flow of volume in four operating modes of the device. In FIG. 11, as in FIGS. 12–14, the filter/reservoir 28 is filled from a source of volume. The volume to be pumped through the system may be supplied to the device from a variety of containers or methods to keep the filter/reservoir 28 at any desired level.

The objective of the mode of operation illustrated in FIG. 11 is to purge the system of air. The filter/reservoir outlet 28B is connected directly to the pump 22, and volume flows from the outlet port 28B through the line 29 fed through the pump. The outlet of line 29 from pump 22 is connected directly to inlet port 30A of the heat exchange component 30. Flow is developed by the action of roller pump 22 as the rollers 26 impinge on line 29 forcing volume therethrough. The two-way by-pass to patient valve 34 is closed to the patient and closed to the purge-by-pass line 36.

The purge-by-pass two-way valve 31 is opened to the filter/reservoir 28, and open to the air purge position, to allow the evacuation of air via line 32 and reservoir vent 43. The duration of this mode of operation is for a period sufficient to make the system air free.

This mode of operation is a further safety procedure and prevents the infusion of air to the patient.

Figure 12:
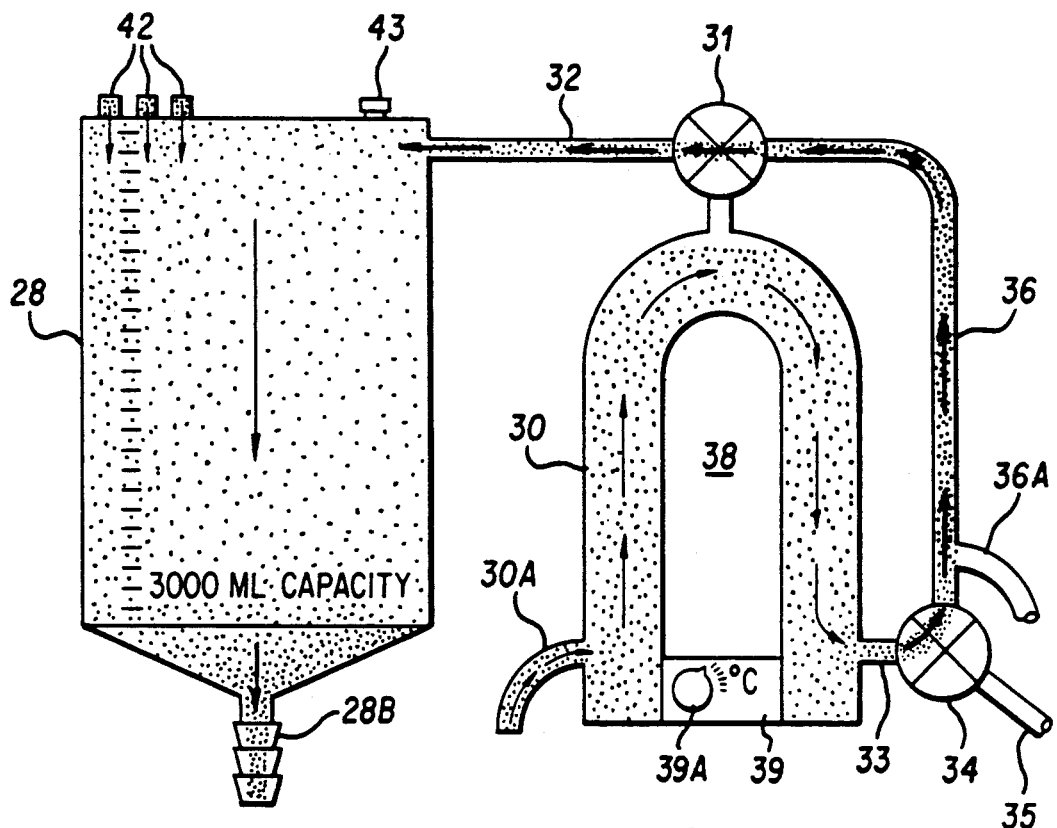
FIG. 12 illustrates the flow of volume during the by-pass mode of operation.

Referring now to FIG. 12, there is shown the flow of volume during the by-pass mode. This mode of operation normally follows the system purge procedure illustrated in FIG. 11 and is also preliminary to the operation of the device, i.e., volume to patient.

The filter/reservoir 28 is filled from the volume source and flow follows its normal course from the roller pump 22 and into the inlet port 30A of heat exchange component 30. Heat exchange component 30 has been set at the desired temperature setting. Two-way by-pass to patient valve 34 is closed to the patient and opened to the filter/reservoir 28, and volume is continuously recirculated until the device is ready for use, i.e., until the volume has been heated to the desired temperature. This mode is another very desirable safety feature since it raises the temperature of refrigerated or ambient temperature volume to body temperature before it is infused to the patient thereby avoiding a shock effect to the patient which would be caused by sub-body temperature volume.

Figure 13:
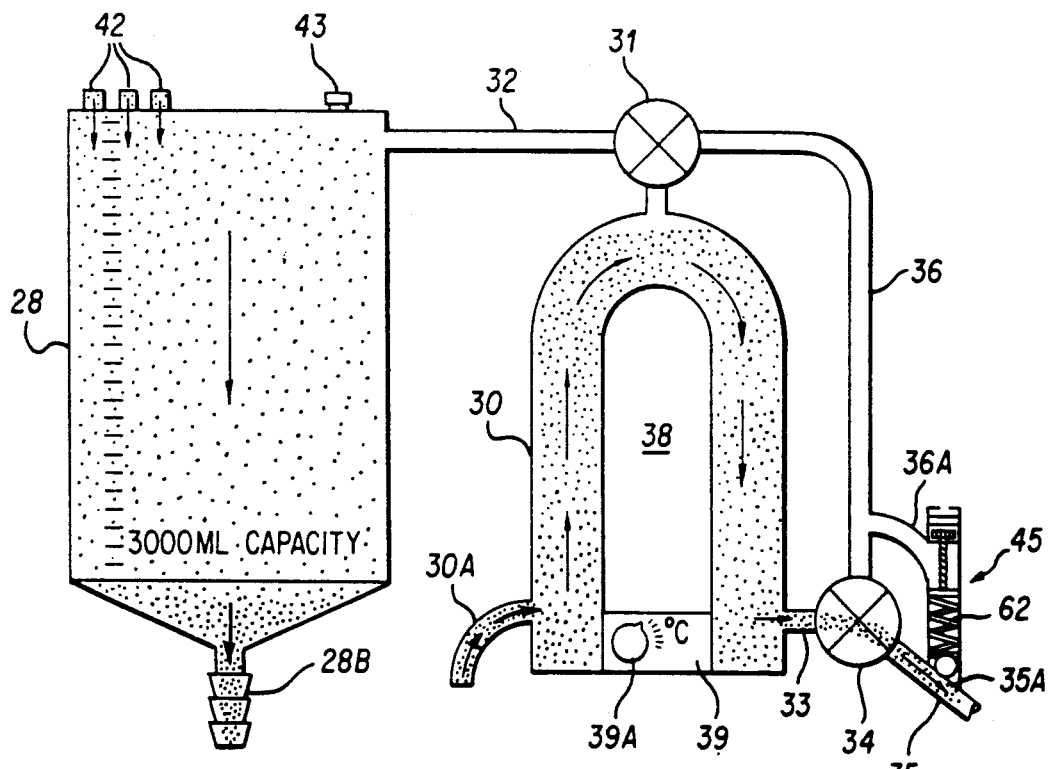
FIG. 13 illustrates the normal mode of operation of the RID with volume flow to patient.

Referring now to FIG. 13, the normal mode of operation of RID 10 may be seen with the path of volume flow to the patient. This mode of operation, as illustrated in FIG. 13, follows the purge procedure and the recirculation procedure for warming volume to the desired temperature. The filter/reservoir 28 is filled from the volume source and flows from outlet port 28B of the filter/reservoir 28 through the pump to the inlet port 30A of heat exchange component 30. The by-pass-to-patient valve 34 is opened to the patient and closed to the purge by-pass line 36 and pressure control valve 45 is also closed due to bias of spring 62 on ball 63, keeping ball 63 on its seat 35A.

Figure 14:
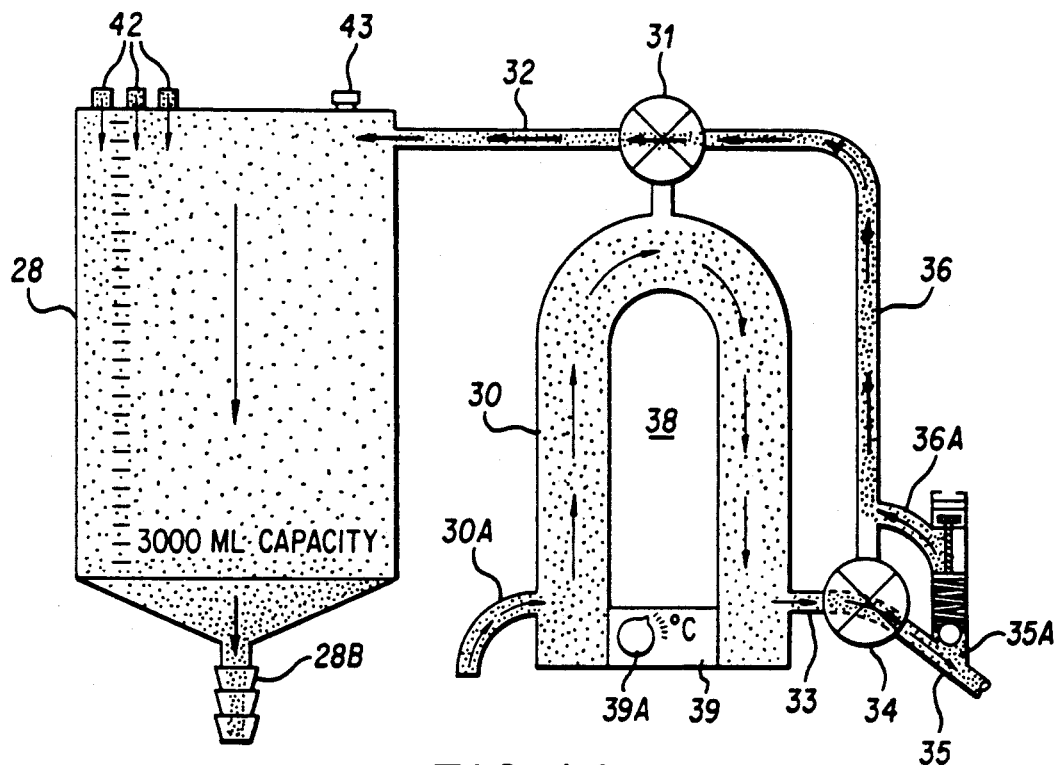
FIG. 14 illustrates the flow of volume to patient with the pressure control valve open.

Referring now to FIG. 14, there is shown the flow path of volume when there is an increase of back pressure in the volume pathway to the patient. As indicated previously spring loaded pressure control valve 45 is normally closed during all modes of operation. In FIG. 14, normal flow to patient is depicted with pressure control valve 45 open. This valve is a further safety feature and is positioned in the system to sense an overpressure condition to the patient. When pressure is too great to the patient, i.e., higher than the range set for the valve 45, 230–300 mm Hg, the valve 45 will release back pressure from the patient. When valve 45 is opened, volume will flow into the purge by-pass line 36A and return to the filter/reservoir 28 for recirculation via lines 36 and 32. In this event, the operator would adjust the pressure to the patient by reducing the rpm of pump 22 or reset the spring loaded pressure control valve 45 to a new setting, whichever is indicated. The spring loaded pressure control valve 45 is a safety device which prevents elevated perfusion pressure to the patient.

Having described the various components of the rapid infusion device 10, the set-up and assembly of the RID 10 is as follows: Attach heater element 38 to pump housing 21 through the use of mounting bracket 37 which is attached to pump housing 21 by a first pair of bolts and a second pair of bolts for securing heater element 38 to bracket 37. Next, place the new disposable unit 50 which includes filter/reservoir 28 and heat exchange component 30 with their associated pathways and valves, on top of roller pump aligning the female inverted "U" of heat exchange component 30 with the male inverted "U" of heating element 38. Ensure good surface contact between the walls of these two units. The fit of the units will be sufficient to provide stability for these disposable components when seated in position on roller pump 22. Attach PVC line 29 to outlet port 28B of filter/reservoir 28. Place the other end of PVC line 29 into pump raceway 23 and secure in place, then attach the free end of line 29 to stem portion 30A of heat exchange component 30. Connect power cord 40 of heating element 38 to the auxiliary power outlet in the right side of control panel 12 as indicated by plug 41 in FIG. 1. Attach the catheter to the line to patient line 35 by engaging the male luer lock provided for this purpose.

When the disposable components have been properly placed with respect to the permanent components of RID 10 and the appropriate pathways have been connected as required, the RID 10 is ready for the pre-operating checks which include the following:

1. Check the connections at the filter/reservoir exit port 28B and heater unit inlet port 30A.
2. Rotate purge-by-pass valve 31 and by-pass-to-patient valve 34 to insure freedom of movement in the valves 31 and 34.
3. Check all power connections. Assure proper grounding.
4. Check air vent screw cap 43A for freedom of movement.
5. Check PVC line 29 for proper positioning in track raceway 23, 23A, of pump 22.
6. Check the setting on Spring Loaded Pressure control valve 45 for a range of 230–300 mm Hg.

After the pre-operating procedural checks have been made and each item is found to be in good working order, a review of the operating modes of RID 10 in the order of undertaking may be seen to include:

A. System Purge

1. Loosen Air vent cap 43A.
2. Turn Purge-by-pass Valve 31 to the purge position.
3. Turn By-Pass-To-Patient Valve 34 to the closed position.
4. Turn heater unit thermostat 39 to the OFF position.
5. Commence flow of volume to the filter/reservoir 28 from the volume supply source.
6. Allow the filter/reservoir 28 to fill to at least 200 ml or alternative amount to be pumped.
7. Turn the on/off switch 17 to the ON position.
8. Place AC/DC selection switch 18 in the AC position.
9. Place the Stop/Forward switch 19 in the FORWARD position.
10. Leave the RPM control knob 14 in the ZERO setting until flow is desired in the system.
11. Rotate RPM control knob 14 forward to start the rotation of the pump's rollers 26 in the raceway formed by wall 23.
12. Continue this mode of operation until the system is free of air.

B. By-Pass Mode (Recirculation)

1. This mode of operation normally follows the preceding system purge operation. At this time the volume to be infused fills the system and has been purged of air.
2. The various steps required for this mode are as follows:
   a. Turn the Purge-By-Pass valve 31 to the by-pass position.
   b. Turn the thermostat setting knob 39A to the desired setting.
   c. Turn the By-Pass-To-Patient valve 34 to the by-pass position.
   d. Rotate the RPM knob 14 forward to restart the flow. Continue this mode of operation until the volume has been heated to above 37 degrees C. or a higher alternative temperature.

C. Volume To Patient (Normal Operation)

1. This mode is considered to be the normal mode of operation. This mode follows the purge and recirculation modes.
2. The various steps required for this mode are as follows:
   a. Attach the catheter line (not shown) to patient.
   b. Check the setting on the Spring Loaded Pressure Control Valve 45.
   c. Open By-Pass-To-Patient Valve 34 to the patient and monitor patient and volume level in the RID 10.

D. Volume To Patient (Pressure Control Valve Open)

This condition will only occur during the normal volume to patient operation of the RID 10. The Spring Loaded Pressure Control Valve 45 will open allowing the volume to move up the Purge By-Pass line 36 toward the filter/reservoir 28 if the pressure to patient exceeds the predetermined limit. Two steps may be taken to remedy this condition. (1) Reduce the RPM of roller pump 22 by turning RPM knob 14 counterclockwise or adjust Spring-Loaded Pressure Control Valve 45 to a new setting.

Following modes C or D, the disconnect procedure is as follows:

A. Disconnect exit line 35 to patient (DISPOSE).
B. Remove connecting line 29 from filter/reservoir 28 to heater unit 30 (DISPOSE).
C. Turn heat exchange unit thermostat knob 39A to the OFF position.
D. Lift the disposable components, i.e., filter/reservoir 28, heater unit 30, and flow lines 32, 36 off the top of roller pump 22 (DISPOSE).
E. Set aside a new sterile set of disposable parts for the next use of RID 10.
F. Turn all controls to the OFF position and unplug the plug 41.

Roller pump 22 is a standard industrial roller pump commonly found in hospital applications of a various nature, but normally those applications which require the movement of liquids at a modulated rate. Any pump of similar capability may be used in conjunction with the disposable components and other disposable parts of the RID.

While the invention has been described in its preferred embodiment, it is to be understood that the words which have been used are words of description rather than limitation and that changes may be made within the purview of the appended claims without departing from the full scope or spirit of the invention.

What is claimed is:

1. A rapid infusion system for rapidly delivering filtered, bubble free, warmed volume to a patient, said rapid infusion device comprising in combination:
   (a) a pre-assembled unitary disposable unit; and
   (b) a permanent durable unit;
   wherein said disposable unit includes all sub-components that will come into contact with the volume infused to the patient including a disposable flexible length of tubing serving as a pumping chamber;
   wherein said permanent durable unit includes reusable components including driving means and related control means therefor, pump means operably connected to said drive means, heating means for heating the volume, and housing means, said flexible tubing having opposite ends thereof connected to said pre-assembled unitary disposable unit whereby said disposable unit and said length of tubing can be disposed of after use;

wherein said housing means supports said pump means, said unitary disposable unit, flexible tubing, said heating means, said drive means, and said related control means whereby a filtered, bubble free warmed volume of predetermined temperature may be infused to a patient at a predetermined flow rate;

wherein said preassembled unitary disposable unit comprises a reservoir, said reservoir having an upper end and a plurality of supply inlets, a return port, an outlet and an air purge vent adjacent said upper end, said vent being operative to remove air from the system prior to infusing the pumped volume to a patient, said reservoir further including baffle means which is positioned below said plurality of supply inlets and said return port and filter means mounted within said reservoir whereby the volume to be infused can be filtered, de-aerated and warmed prior to the infusion; and wherein said filter means comprises a two stage filter with the first stage serving to remove particles in excess of 150 microns from said volume and said second stage is a multi-layered wafer assembly of filtering material which removes any impurities of 27–40 microns in size.

2. A rapid infusion system of the character defined in claim 1, wherein said supply inlets extend adjacent one side of said reservoir providing a fill side and said first stage filter is a coarse sponge plastic material positioned adjacent said supply inlets on the fill side of said reservoir.

3. A rapid infusion system of the character defined in claim 1, wherein said multi-layered wafer assembly comprises three layers of filtering material; the first layer consisting of nylon mesh, followed by a layer of fibrous cotton material and a subsequent layer of nylon mesh with both stages of said filter means being supported by a filter frame within said reservoir.

4. A rapid infusion system for rapidly delivering filtered, bubble free, warmed volume to a patient, said rapid infusion device comprising in combination:

(a) a pre-assembled unitary disposable unit; and
(b) a permanent durable unit;

wherein said disposable unit includes all sub-components that will come into contact with the volume infused to the patient including a disposable flexible length of tubing serving as a pumping chamber;

wherein said permanent durable unit includes reusable components including driving means and related control means therefor, pump means operably connected to said drive means, heating means for heating the volume, and housing means, said flexible tubing having opposite ends thereof connected to said pre-assembled unitary disposable unit whereby said disposable unit and said length of tubing can be disposed of after use;

wherein said housing means supports said pump means, said unitary disposable unit, flexible tubing, said heating means, said drive means, and said related control means whereby a filtered, bubble free warmed volume of predetermined temperature may be infused to a patient at a predetermined flow rate;

wherein said preassembled unitary disposable unit further includes a pair of manually operable two-way valves and an adjustable pressure controlled by-pass valve;

wherein said adjustable pressure controlled by-pass valve includes a cylindrical housing which encloses a spring loaded ball valve and an adjusting screw which can be adjusted to set the spring bias on said ball valve with respect to a cooperating seat whereby a patient line pressure in excess of the predetermined setting forces said ball to unseat and by-pass a portion of said volume back to said reservoir; and wherein said predetermined setting is in the range of 230 to 300 mm Hg.

5. A rapid infusion system for rapid delivery of filtered, bubble free, warmed volume to a patient, said rapid infusion system comprising a preassembled unitary disposable subsystem, a permanent reusable subsystem and a disposable length of PVC tubing which serves as a pumping chamber and interconnects portions of said preassembled unitary disposable subsystem; said preassembled unitary subsystem comprising reservoir means with filter means mounted therein, heat exchange unit means and volume pathways including valve means; said disposable length of PVC tubing having opposite ends interconnected with said reservoir means and said heat exchange unit means at opposite ends thereof; said permanent reusable subsystem comprising motor drive means and first housing means enclosing said motor drive means and including control panel means; second housing means mounted on top of said first housing means; pump means and heater element means mounted on said second housing means; said second housing means serving as a supporting base for said preassembled unitary disposable subsystem whereby any desired volume may be infused rapidly into a patient; and wherein said reservoir means, said heat exchange unit means, and said volume pathways of said disposable subsystem are formed simultaneously through joining of two halves after which said filter means are placed in said reservoir means, said two halves are then joined and sealed for liquid integrity.

6. A rapid infusion system for rapid delivery of filtered, bubble free, warmed volume to a patient, said rapid infusion system comprising a preassembled unitary disposable subsystem, a permanent reusable subsystem and a disposable length of PVC tubing which serves as a pumping chamber and interconnects portions of said preassembled unitary disposable subsystem; said preassembled unitary subsystem comprising reservoir means with filter means mounted therein, heat exchange unit means and volume pathways including valve means; said disposable length of PVC tubing having opposite ends interconnected with said reservoir means and said heat exchange unit means at opposite ends thereof; said permanent reusable subsystem comprising motor drive means and first housing means enclosing said motor drive means and including control panel means; second housing means mounted on top of said first housing means; pump means and heater element means mounted on said second housing means; said second housing means serving as a supporting base for said preassembled unitary disposable subsystem whereby any desired volume may be infused rapidly into a patient; and wherein said filter means comprises a two stage system wherein said first stage is a coarse filter formed by a coarse plastic material which removes material over 100-150 microns in size; said second stage serving as the fine filter removing impurities in the 27 to 40 micron size.

7. A rapid infusion system of the character defined in claim 6, wherein said second stage of said filter means comprises a three layered filter in wafer form, firstly, a layer of nylon mesh, secondly, a layer of fibrous cotton material, and thirdly, a second layer of nylon mesh whereby filtration down to 27 to 40 micron size is accomplished.

8. A rapid infusion system for rapid delivery of filtered, bubble free, warmed volume to a patient comprising an integral disposable unit which includes all subcomponents that come into contact with the volume infused to a patient, a permanent durable unit which comprises the reusable components including drive means operably connected to pump means; heater means and associated controls therefor, and a disposable length of flexible tubing which serves as the pumping chamber of said pump means and interconnects pathways of said integral disposable unit whereby a warm, filtered, bubble free volume of blood or other fluid may be rapidly infused into a patient by a single medical person;

wherein said integral disposable unit further includes a pair of manual two-way valves and an adjustable spring loaded pressure control valve, said pair of manual two-way valves mounted in volume pathways whereby said two-way valves can be set to direct volume back to said reservoir when operating the device in its de-aerating and warming modes;

wherein said adjustable spring loaded pressure control valve further includes a cylindrical housing in which said spring loaded valve is mounted, said cylindrical housing enclosing an adjusting screw, stationary disc with a threaded aperture, coil spring and ball valve whereby said adjusting screw biases said coil spring into contact with said ball valve to maintain it closed until a predetermined pressure is reached; and wherein said predetermined normal pressure setting of said adjusting screw is in the range of 230-300 mm Hg.

* * * * *